United States Patent [19]

Herman et al.

[11] 4,270,977

[45] Jun. 2, 1981

[54] PROCESS FOR PREPARING WATER SORPTIVE PRODUCTS

[75] Inventors: Daniel F. Herman, Princeton; Uno Kruse, Neptune, both of N.J.

[73] Assignee: NL Industries, Inc., New York, N.Y.

[21] Appl. No.: 90,207

[22] Filed: Nov. 1, 1979

[51] Int. Cl.$^3$ .......................... D21H 3/44; D21D 3/00; C08F 220/20

[52] U.S. Cl. ................. 162/168 R; 128/263; 128/284; 260/17.4 CL; 260/29.6 H

[58] Field of Search ............. 260/17.4 CL; 162/168 R

[56] References Cited

U.S. PATENT DOCUMENTS

| | | | |
|---|---|---|---|
| 2,798,053 | 7/1957 | Brown | 526/317 X |
| 4,049,491 | 9/1977 | Brandon | 162/101 |
| 4,062,817 | 12/1977 | Westerman | 260/17.45 G |
| 4,104,214 | 8/1978 | Meierhoefer | 260/17.4 CL |
| 4,136,697 | 1/1979 | Smith | 128/285 |

*Primary Examiner*—C. A. Henderson
*Attorney, Agent, or Firm*—Gary M. Nath

[57] ABSTRACT

The present invention is directed to a process for preparing cellulose containing water sorptive products from an aqueous suspension or paper furnish in accordance with conventional paper making techniques. The suspension or paper furnish employed in preparing the sorptive products comprises a polymer component and a fibrous component slurried in water. The polymer component is provided from a specifically defined class of crosslinked copolymers which contain carboxyl groups. A representative polymer from this class includes that obtained by reacting methyl acrylate and methacrylate acid in the presence of ethylene glycol dimethacrylate. The polymer component becomes water sorptive when the carboxyl groups present thereon are neutralized with a base. In the practice of the process of the present invention, a composite product is prepared from the above mentioned suspension, partially dried, and then neutralized in a specifically controlled manner. Neutralization is achieved while controlling the amount of base and water which contacts the composite product. The control is exercised in a manner sufficient to achieve a proper degree of salting and to prevent undue sorption of the water during neutralization. Such control results in a substantial improvement in the cost efficiency of the process since the amount of water which must be eventually evaporated from the neutralized product is held to a minimum.

9 Claims, No Drawings

PROCESS FOR PREPARING WATER SORPTIVE PRODUCTS

BACKGROUND OF THE INVENTION

This invention relates to a process for preparing water swellable sorptive composite products which is adaptable to conventional paper making equipment.

It is well known that a variety of different polymers and polymer forming systems can modify and enhance the water sorptive properties of substances such as cellulose. Such water swellable polymers and systems employing such polymers are illustrated by U.S. Pat. Nos. 3,670,731; 3,954,721; 3,959,569; 3,980,663; 3,989,586; 4,041,020; 4,041,228; 4,041,231. The methods available for employing any of these polymer systems in preparing water sorptive products are controlled in large part by the properties which these systems possess at the time they are utilized.

Typically, the water swellable polymers disclosed in the above mentioned patents possess acid groups which are converted by reaction with base to the salt form before the water sorbing properties are imparted thereto. Thus, in those instances where the salt form of the polymer is produced during polymer preparation or immediately thereafter such polymers cannot be economically employed as additives to cellulose pulp slurries in a paper making process using conventional paper making equipment, e.g. a Fourdrinier, cylinder machine or Rotoformer. This results from the fact that use of a polymer in its highly swellable salt form ensures that it will likely sorb many times its weight in water. Consequently, a substantial fraction of the total water in the paper furnish or stock will be bound in the polymer which is incorporated therein and the wet sheet coming off the Fourdrinier wire or press section can contain as much as 100 pounds of water per pound of polymer. Drying of such a sheet would be prohibitively expensive. By comparison conventional paper manufacture involves evaporation of only about 2 to about 4 pounds of water per pound of paper. For a process to be economical the amount of water to be evaporated should be as close as possible to this range and should be no more than about 10 times the weight of the paper.

The problem of moisture control in a paper making process is implicitly recognized in U.S. Pat. No. 3,989,586 and is solved by postponing the conversion of the potentially water swellable copolymer disclosed therein, i.e. a crosslinked, water insoluble copolymer of maleic anhydride and a vinyl monomer, until after the paper sheet containing said copolymer has been dried. Even then, the neutralization is carried out with a substantially anhydrous alkaline agent such as ammonia gas or an alcoholic solution containing a base. While the use of an anhydrous alkaline agent prevents undue sorption of water prior to drying the paper sheet, such an approach is accompanied by its own set of problems. For example, ammonia gas is very toxic and special provisions must be made for its containment. Since conventional paper making machines are typically unsealed, the use of ammonia gas is commercially unfeasable. Furthermore, the use of alcohol as a solvent for the base is very expensive relative to basic aqueous solutions.

It would therefore be a distinct advantage if a method could be developed for making water sorptive products which is capable of preventing undue moisture sorption during neutralization of the water swellable polymer with an aqueous alkaline solution. This would allow one to employ conventional paper making equipment and improve the cost efficiency of the process.

However, in addition to the problems described above, the development of such a method is further complicated by the requirement that when the potentially water swellable polymer is advantageously applied as a solid to the cellulose fibers it must adhere strongly thereto during the paper making process and must remain in the solid state even after neutralization. When neutralization is achieved with an aqueous alkaline solution, many potentially water swellable polymers, while insoluble in their acid form, completely dissolve when converted to their salt form due to the sorption of water.

For example, it has been noted by Verbrugge in an article entitled "Mechanism of Alkali Thickening of Acid-Containing Emulsion Polymers" reported in the *Journal of Applied Polymer Science*, Vol. 14, pages 897 to 928, 1970, that acid containing latexes during neutralization all undergo a common swelling process leading to complete solubilization for the more hydrophilic polymers. Verbrugge described specific neutralization reactions in a series of polymers of varying Tg and hydrophilicity of the general formula methyl methacrylate/ethyl acrylate/methacrylic acid (MMA/EA/MAA) utilizing 20 mole % of MAA and varying ratios of MMA/EA from 50/0 to 0/80. Observations were made of both viscosity changes and visual changes in a light microscope. Work is also disclosed at the higher hydrophilic range of monomer, e.g., utilizing high EA/MAA contents such as 80/20 and 70/30 EA/MAA with zero MMA. The light microscope shows gradual swelling of the particles as the carboxylic acid groups were progressively neutralized. At 80% neutralization, the particles are disclosed as being so highly swollen as to make the phase change from solid to liquid medium barely distinguishable. At 90% and 100% neutralization, the particles are gone and a true solution is formed. Polymer latex particles which are less hydrophilic, e.g., those observed from high MMA levels and lower EA and MAA, e.g., 60/20/20 MMA/EA/MAA, result in viscous gels upon neutralization and are seen in the light microscope as barely discernable swollen gel particles with no clear boundary between the swollen particle and the solution. Electron microscope examination of the dried 100% neutralized latex particle shows numerous tentacles projecting from the central core which result in association or sticking together of particles which in turn result in high viscosity.

When solid particles of potentially water soluble polymers are deposited on cellulose fibers during a paper making process and then subsequently dissolved upon neutralization the paper tends to stick to the rollers which increases the chances that the sheet will break. Furthermore soluble polymers will initially form highly viscous gelled regions within the paper which will seal the paper pores and inhibit further water sorption. Upon still further contact with water the soluble polymer will be leached from the paper sheet causing contamination of the surrounding regions.

Thus, the search has continued for an economic process for making water sorptive paper products wherein conventional paper making equipment can be employed, said paper products relying on the presence of water swellable polymers for their sorptive properties. The present invention is a result of this search.

SUMMARY OF THE INVENTION

In one aspect of the present invention there is provided a process for preparing a water sorptive product. In accordance with this process an aqueous suspension comprising a slurry of a polymer component and a fibrous component in water is formed. The polymer component of the suspension comprises the reaction product of from about 15% to about 50% by weight of an olefinically-unsaturated carboxylic acid, from about 49.07% to about 82% by weight of an alkyl acrylate wherein the alkyl group has from 1 to 6 carbon atoms, and from about 0.03% to about 3.0% by weight of a crosslinking agent. The reaction product has carboxyl groups present thereon which when converted to their salt form impart the capability to said polymer component of sorbing water upon contact therewith. The fibrous component of the suspension comprises at least 50% by weight of cellulosic material. The weight ratio of the polymer component to the fibrous component in the suspension is controlled to be from about 90:10 to about 5:95. A composite product is then formed from said suspension. The composite product is partially dried to reduce the moisture content thereof to between about 3 and about 25%, by weight. The partially dried composite product is then contacted with an amount of an aqueous solution of a base sufficient to achieve a degree of salting of the polymer component in the composite product of from about 100 to about 120% to neutralize the carboxyl groups present thereon, and in a manner sufficient to prevent the weight ratio of the dry neutralized composite product to water sorbed therein during neutralization from exceeding 1:10. The neutralized composite product is then dried to reduce the moisture content thereof to not greater than about 25% by weight.

In another aspect of the present invention there is provided a process for preparing a composite sheet having water sorptive properties. In accordance with this process a suspension comprising a slurry of a polymer component and a fibrous component in water is deposited on a liquid permeable support to form a wet-laid web. The polymer component and the fibrous component of the suspension is the same as described above. The wet-laid web is passed through a drying zone wherein the moisture content is reduced to between about 3 and about 25% by weight thereof. The wet-laid web is then passed through a neutralizing zone wherein it is contacted with an aqueous alkaline solution containing a base in an amount sufficient to achieve a degree of salting of the polymer component of from about 100 to about 120% to thereby neutralize the carboxyl groups present thereon causing the polymer component to swell from sorption of water. The thickness of the neutralized wet-laid web is sensed with a sensing means as it exits the neutralizing zone, and the rate of travel of said wet-laid web through the neutralizing zone is controlled in response to the sensed wet-laid web thickness in a manner sufficient to prevent the weight ratio of the dry neutralized wet-laid web to water sorbed therein immediately after exiting the neutralization zone from exceeding 1:10. The neutralized wet-laid web is then passed through a drying zone wherein the moisture content thereof is controlled to be not greater than about 25% by weight.

DESCRIPTION OF THE PREFERRED EMBODIMENTS

According to the process of the present invention an aqueous suspension, referred to herein as a "furnish", comprising a slurry of a polymer component and a fibrous component in water is formed into a composite product such as by feeding it to a screen or other web forming device employed in conventional paper making operation.

The polymer component of the suspension comprises the potentially water swellable polymer disclosed and claimed in a related U.S. patent application Ser. No. 56,564, filed on July 11, 1979 of Daniel F. Herman and Uno Kruse, the disclosure of which is herein incorporated by reference.

More specifically, the potentially water swellable polymer is the reaction product of a mixture of (a) an olefinically-unsaturated carboxylic acid; (b) an alkyl acrylate; and (c) a crosslinking agent.

Thus, in the production of the potentially water-swellable polymers employed in the process of this invention, a monomeric mixture which contains an olefinically-unsaturated carboxylic acid and an alkyl acrylate is polymerized in the presence of minor amounts of a vinyl crosslinking agent. Crosslinking is achieved by free radical addition polymerization which introduces the vinyl groups of the crosslinking agent directly into the carbon-carbon backbone of the polymer. Where long term resistance to degradation is required, hydrolytically stable crosslinking agents such as divinyl benzene or triallylcyanurate may be employed.

The olefinically-unsaturated carboxylic acids useful in preparing the potentially water swellable polymers employed in the process of the present invention are those materials containing an activated carbon-to-carbon olefinic double bond and at least one carboxyl group, that is, an acid containing an olefinic double bond. Representative examples of suitable carboxylic acids include acrylic acid, methacrylic acid, ethacrylic acid, crotonic acid, muconic acid, aconitic acid and similar compounds as well as mixtures thereof. The preferred carboxylic acids are acrylic acid and methacrylic acid.

The alkyl acrylates useful in preparing the potentially water swellable polymer are those alkyl acrylates wherein the alkyl groups have from 1 to 6 carbon atoms and preferably 1 to 4 carbon atoms. Representative examples of suitable acrylates include methyl acrylate, ethyl acrylate, propyl acrylate, n-butyl acrylate and iso-butyl acrylate.

The preferred acrylates are methyl acrylate, ethyl acrylate and n-butyl acrylate with methyl acrylate being most preferred. Higher chained acrylates have a tendency to become hydrophobic causing the final polymer salt to exhibit lower swelling and water sorption in water and saline solutions.

Other monomers, which do not fall within the description of the monomers described above may be employed in minor amounts, that is up to about 8% by weight, provided they do not adversely affect the basic and novel characteristics of the process of this invention. For example, acrylamide, 2-ethylhexyl acrylate, hydroxylethyl acrylate and hydroxylethyl methacrylate may be employed as partial replacement for methyl acrylate or ethyl acrylate, and itaconic acid, maleic acid or maleic anhydride employed as partial replacement for methacrylic acid or acrylic acid.

The free radical addition polymerization crosslinking technique employed in the preparation of the potentially water swellable polymers is well known in the art. Suitable crosslinking agents include polyunsaturated polymerizable vinyl monomers containing two or more free radical polymerizable ethylenic groups. Substantially any monomer having more than one polymerizable ethylene group can be used which monomer must be able to enter into vinyl addition polymerization reactions with the foregoing mentioned acids and acrylates. Illustrative examples of crosslinking agents include:

(1) diacrylate esters and dimethacrylate esters of glycols such as ethylene glycol dimethacrylate, propylene glycol dimethacrylate, butylene glycol dimethacrylate and hexylene glycol dimethacrylate;

(2) diacrylate esters and dimethacrylate esters of ether or polyether glycols such as diethylene glycol diacrylate, diethylene glycol dimethacrylate, triethylene or tetraethylene glycol diacrylate and triethylene or tetraethylene glycol dimethacrylate;

(3) allyl esters of polymerizable unsaturated carboxylic acids such as allyl acrylate, methallyl acrylate, allyl methacrylate, allyl ethacrylate, ethallyl acrylate, methallyl methacrylate;

(4) di or trivinyl aromatic compounds such as divinyl benzene, and trivinyl benzene;

(5) di or triallyl esters of di and tribasic acids such as diallyl phthalate, triallyl cyanurate, diallyl maleate, diallyl succinate, triallyl phosphate, diallyl oxalate, diallyl malonate, diallyl citrate, diallyl fumarate, diallyl ether; and (6) acrylate or methacrylate esters of polyols such as di or triacrylate or methacrylate esters of trimethylol ethane, trimethylol propane, or pentaerythritol.

In order to achieve the desired polymer properties, it is important that the monomers be polymerized together in certain specified proportions, although the exact proportions will vary depending on the polymer characteristics desired.

The olefinically-unsaturated carboxylic acids of the polymer are employed in amounts of from about 20% to about 40% by weight, based on the total weight of the monomers used.

If the amount of carboxylic acid employed exceeds about 50% by weight, the resulting polymer when converted to its salt form becomes excessively hydrophilic while sorbing excessive amounts of water leading to a (1) soluble polymer, (2) viscous solution or suspension, and (3) loss of polymeric structural integrity. If the amount of carboxylic acid is less than about 15%, the resulting polymer salt is insufficiently hydrophilic and exhibits poor water sorption.

The alkyl acrylates are employed in amounts of about 49.07 to about 78% by weight, based on the total weight of the monomers used.

If the amount of the acrylate employed exceeds about 82% by weight, then the resulting polymer when converted to its salt form is insufficiently hydrophilic and exhibits poor water sorption. If the amount of acrylate is less than about 49.07%, the resulting polymer becomes excessively hydrophilic while sorbing excessive amounts of water leading to a (1) soluble polymer, (2) viscous solution or suspension, and (3) loss of polymeric structural integrity.

The amount of crosslinking agent employed is desirably limited to an amount from about 0.03 to about 3.0% by weight, preferably from about 0.08 to about 2.0%. This low amount of crosslinking agent has been found sufficient to render the polymer water-insoluble when converted to its salt form, while retaining a high degree of water absorbency.

Use of less than 0.03% results in a polymer which upon neutralization functions primarily as a thickening agent lacking discrete particle identity. As the amount of crosslinking agent is increased above 0.03% the more discrete and rigid the resulting polymer becomes rendering expansion of the salt particles derived therefrom less possible. Water sorbency drops to a commercially unacceptable level when amounts greater than 3.0% crosslinking agent are used.

The preferred polymer is prepared from a mixture containing as essential ingredients from about 20 to about 40% by weight of an olefinically-unsaturated carboxylic acid selected from methacrylic acid, acrylic acid and mixtures thereof; from about 59.02 to about 78% by weight of an alkyl acrylate selected from methyl acrylate, ethyl acrylate, n-butyl acrylate, and mixtures thereof and from about 0.08 to about 2.0%, by weight, of a crosslinking agent, preferably ethylene glycol dimethacrylate.

The monomer constituents of the polymer should be reacted as completely as possible during polymerization. The polymer may be made by conventional polymerization techniques such as by solution, suspension or emulsion polymerization on a batch, continuous or semi-continuous basis.

Suspension polymerization is preferred since this technique results in an acid polymer product in the form of a high surface area granular precipitate having an average particle size between 50 and 400 microns, (e.g. between 50 and 100 microns), which product appears to be composed of accretions of small particles in the 1 to 50 micron range. A large proportion of these smaller particles appear as high surface area donuts of collapsed spherical shapes with 2 to 5 micron protuberances on their surfaces.

The polymerization reaction is carried out in the presence of a catalyst. The catalysts which form free radicals necessary for the reaction are conventional and are usually organic peroxides, inorganic persulfates and free radical generating azo compounds. The amount of catalyst used is normally from about 0.01 to about 2.0 parts by weight per 100 parts by weight of the total monomeric material to be reacted. Representative examples or organic peroxides include benzoyl peroxide, acetyl peroxide, bis(p-bromobenzoyl)peroxide, di-t butyl peroxide, t-butyl hydroperoxide, dicumyl peroxide, cumene hydroperoxide, bis(p-methoxybenzoyl)-peroxide, 2,2'-azobisisobutyronitrile and the like. Exemplary inorganic persulfates include ammonium, sodium and potassium persulfates. These may be used alone or in conjunction with sodium or potassium bisulfite. While polymerization is preferably carried out with a free radical catalyst, radiation induced polymerization can also be employed such as high energy X-rays or gamma rays.

Suitable conventionally employed surface active agents and/or colloids may also be used during the polymerization reactions.

Polymerization times, and temperatures may vary considerably depending on the monomer system and catalyst used. The polymerization reaction will generally be completed within at least 30 minutes to several hours at temperatures from about 0° to about 100° C.

and prefereably within 1 to 4 hours at 65° to 90° C. for maximum efficiency.

Preferably the suspension polymerization is conducted by charging a reactor with deionized water and a suspension agent and deaerating with an inert gas. The reactor may be optionally heated to dissolve the suspension agent. Previously determined amounts of olefinically-unsaturated carboxylic acid and alkyl acrylate are added either separately or in admixture. Addition may occur at room temperature or at the reaction temperature. The crosslinking agent and catalyst may be added simultaneously with the monomer mixture or separately.

The reactor contents are then agitated by conventional means and heated to commence polymerization at a temperature around the lowest boiling point of the monomers. When methyl acrylate is polymerized, this temperature is about 70° C. The reaction is then allowed to continue to polymerize to completion whereupon the reactor contents are cooled. The polymer product may be alternately recovered from the slurry by conventional filtration means. The final product slurry can be steam treated at about 100° C. to remove any traces of unreacted monomers. Alternately, a highly reactive redox catalyst is added to essentially provide a 100% yield. The slurry can then be filtered to recover the polymer in its non-swelling acid form. Alternatively, the filtered polymer cake may be redispersed in water and dried, and pulverized.

Typically the solids content of the final reaction product is from about 15% to about 50%. Lower solid contents can be used but are generally undesirable from an economic standpoint.

The polymer product employed in the process of the present invention has an indeterminate "weight average" molecular weight because of its crosslinking and insolubllity in solvents commonly used in the determination of molecular weights. The neutralized polymer is capable of sorbing surrounding water many times its own weight. In doing so, each individual sorbent particle swells or enlarges several times its individual diameter without destruction of the particles' particulate integrity. Sorption of distilled water in amounts greater than $100 \times$ the polymer weight have been noted. In 1% sodium chloride solutions, up to $30 \times$ weight increases have occurred whereas in 15% to 25% sodium chloride solutions up to $10 \times$ weight increases have been noted. This amount of sorption is significant, especially when it is recognized that the polymer particle substantially immobilizes the same therein and the resulting particulate material retains its structural integrity.

The potentially water-swellable polymer produced in the acid form is filtered from its aqueous reaction medium to yield a cake containing between about 40 and about 50% water.

The acid cake is then dispersed in water using a suitable agitator to obtain a slurry of the suspended agglomerate particles and the slurry mixed with an aqueous slurry of the fibrous component or the polymer cake is ground to a fine particle size and mixed as is with the slurried fibrous component.

Alternatively, the original suspension polymerized slurry may be used directly as the polymer component provided that unreacted monomer is stripped completely therefrom.

The fibrous component of the furnish is typically provided from a cellulosic material which may be derived from any species of coniferous hard and soft pulpwood such as spruce, hemlock, fir, pine and others, deciduous pulpwood such as poplar, birch, cottonwood, alder and others as well as from fibrous, nonwoody plants suitable for papermaking, such as cereal straws, bagasse cornstalks, grasses, and the like, and also the usual cellulosic sources such as sulfate and sulfite pulps.

These various fibrous raw materials typically are converted into pulp by way of the conventional pulping procedures during which the material is digested with an aqueous cooking liquor containing the selected pulping agent. Pulps with high aplha cellulose as made by standard industry techniques are particularly useful in the subject process.

In addition to the cellulosic pulp fibers, the fibrous component of the furnish may contain minor amounts, e.g. less than 50%, of other short length, (e.g. from about ⅛ to about ¾ in. length) fibers such as cotton linters, and chopped synthetic fibers such as rayon, polyethylene terephthalate, nylon, and copolymers containing at least 85% acrylonitrile and the like.

The addition of the polymer component to the slurried fibrous component can be made at any convenient point in the paper making machinery circuit, such as, at a stock chest, at a fan pump or in conduits leading to the headbox, provided that sufficient mixing thereof occurs before the resulting furnish is fed to the screen or web forming device.

The weight ratios on a dry basis of the polymer to the fibrous component in the furnish is typically controlled to be from about 90:10 to about 5:95, preferably from about 65:35 to about 15:85, and most preferably from about 50:50 to about 20:80.

Since the polymer component is more expensive than the fibrous component it is generally desirable to employ the least amount of polymer component which will impart the desired water sorptive properties for the particular end use for which the resulting product will be employed.

In addition to the polymer component and the fibrous component, the furnish may also contain alum, resin size and various formation aids such as modified starches typically employed in paper making operations.

The solids content of the furnish containing the fibrous and polymer components can vary over a wide range provided there are sufficient solids to allow formation of a suitable composite product. Typically the solids content of the furnish can vary from about 2 to about 5%, by weight, based on the weight of the furnish.

In accordance with well known paper making techniques the furnish is diluted to a solids content of about 0.02 to about 0.4% and deposited upon a liquid permeable support to form a composite product such as wet-laid web. The solid materials remain on the support while the excess water is allowed to drain off. The diluted furnish may be deposited from a headbox having a means for discharging the slurry at a predetermined rate. The liquid permeable support may be a mesh or gauze of metal or plastic material, for example stainless steel mesh or nylon mesh and is preferably movable relative to the discharge orifice of headbox. For example the liquid permeable support may be in the form of an endless moving belt of plastic or metal mesh or gauze. A Fourdrinier machine is a typical example of such a device. The moving permeable support is commonly referred to as a wire in paper making operations.

Similarly, the furnish can be run into screen molds or the like to produce molded pulp products.

The resulting composite product is then processed and partially dried in a conventional fashion to reduce the moisture content thereof to between about 3 and about 25%, preferably from about 6 to about 20%, and most preferably from about 10 to about 15%, by weight, based on the weight thereof.

A number of methods for reducing the water content of the composite product are available.

For example, the liquid permeable support carrying the deposited furnish can be passed through a series of pressure rolls (e.g., the press roll of paper making machine) producing a plurality of nip actions which progressively squeeze out water therefrom and control its thickness to produce a coherent agglomerated layer, e.g. a wet-laid web, of the desired water content and strength. The water content and thickness of the deposited layer may be controlled by varying the pressure applied by the pressure rolls and by nip setting adjustment. The pressure rolls may be arranged above the deposited layer so as to squeeze the layer between the rolls after it is lifted from the permeable support or wire. In an alternative method of controlling the water content of the furnish or slurry there may be employed a cylinder paper machine which is partly immersed in the furnish and rotated so as to deposit a layer of furnish on its circumference. At one section of the cylinder suction boxes situated under the permeable support or wire remove excess water. The paper is then lifted off the support or wire and enters the press section. Where the agglomerated layer is weak, it may be transferred to a felt support which carries it through the press section and then to the drier.

In another alternative embodiment the composite product can be passed through a drying chamber which can be of any suitable construction. Typically such a chamber is adapted to circulate hot air to carry off water vapor evaporated from the sheet. Steam heated can driers are also commonly employed. Combinations of the above methods can also be employed.

The composite product should not be completely dried since this will hinder the neutralization step by inhibiting rapid sorption of the aqueous alkaline solution.

The particular drying method employed will be selected to impart a wet strength to the composite product so that is possesses sufficient structural integrity that it will not cut, tear, or disintegrate during the neutralization step.

The wet strength of the composite is dependent upon its thickness, density and water content, and in practice, the desired thickness and density can be attained by an appropriate choice of the method of controlling the water content. Thus, if pressure is applied to the deposited agglomerated layer, the density will be increased and the thickness and water content will be reduced. Alternatively, if the water content is reduced by heating, the thickness will be substantially unchanged and the density will be reduced. A few simple experiments will determine what conditions are necessary to achieve a composite product having the desired thickness, density, water content and wet strength so that it may be drawn through the aqueous alkaline solution without tearing.

The density of the composite or product depends primarily upon the density required in the final shaped article but is also controlled to permit ready sorption of the aqueous basic solution employed in the neutralization step.

Generally, low densities in the range of about 0.5 to about 0.75 gm/cc are desirable.

The partially dried composite is then contacted with controlled amounts of an aqueous solution of a base to convert the polymer component to its corresponding salt form.

Any suitable organic or inorganic base which is soluble in water may be used to effect neutralization. Representative bases include sodium hydroxide, potassium hydroxide, lithium hydroxide, ammonium hydroxide, ammonia, and sodium carbonate. Neutralization may also be achieved with organic amines such as ethanolamine, diethanolamine, triethanolamine, methyl diethanolamine, butyl diethanolamine, diethyl amine, dimethyl amine, trimethyl amine, triethyl amine, tributyl amine, and so forth, and mixtures thereof. The most preferred base is sodium hydroxide. In short, any basic material may be used which does not adversely affect the polymer composition.

In order to effect complete neutralization, stoichiometry should be observed between the equivalents of base dissolved in the aqueous alkaline neutralizing solution and the carboxylic acid equivalents in the polymer component of the composite. Thus, at least one equivalent of base, such as sodium hydroxide, per equivalent of carboxylic acid containing monomer moiety should be employed. However, as much as a 20 equivalent percent excess of base may be employed to ensure that all the carboxylic acid groups are reached by the neutralizing solution. In fact, a slight excess is desirable to drive the reaction and ensure the potential to achieve maximum swelling. The excess alkalinity is not harmful since it reacts upon drying by partially saponifying the acrylate ester segments, particularly the methyl acrylate, to yield additional sodium acrylate monomer units in the polymer chain backbone.

For the sake of convenience, the amount of base which is contacted with the partially dried composite can be expressed functionally as that required to achieve a particular degree of salting of the polymer component.

The degree of salting of the polymer component is herein defined to be the number of equivalents of base sufficient to react with the total number of acid equivalents in the polymer component of the composite expressed as a percentage of the total number of acid equivalents present thereon. Thus, a 110% degree of salting indicates that the polymer component has been reacted with a 10% stoichiometric excess of base necessary to convert 100% of the acid groups present thereon to the corresponding salt.

Accordingly, the polymer component of the composite is reacted with sufficient base to achieve a degree of salting of from about 100 to about 120%, and preferably from about 110 to about 120%.

It is critical to the present invention that not only the proper degree of salting be achieved during the neutralizing step but also that the neutralization be achieved while controlling the amount of water sorbed from the aqueous alkaline solution by the composite during neutralization.

It is essential that immediately upon completion of the neutralizing step that the weight ratio of the dry neutralized composite product to water sorbed therein not exceed about 1:10. Weight ratios wherein the amount of sorbed water is greater than about 1:10 would result in undue weakening of the sheet and excessive energy expenditure during drying to remove the unnecessary large amount of sorbed water.

Typically the amount of water sorbed by the composite is controlled to be in the range of dry composite weight to sorbed water weight ratios of about 1:0.5 to 1:5.0 and preferably about 1:1 to about 1:3.5.

Conventional paper sheets before drying could not support such quantities of water without weakening and tearing on the machine. In the practice of the present invention, however, the acid polymer is rapidly neutralized by the base and the resulting polymer salt rapidly sorbs all of the water. Since the amount of water sorbed is controlled to be far below the equilibrium sorption capacity of the polymer salt, the sheet remains essentially dry in appearance and suffers no significant loss in wet strength. It can therefore travel through a second dryer without suffering tears.

When a ratio of less than 1:0.5 with respect to water is sorbed, there is a danger that all of the free water will be rapidly sorbed during neutralization by only a portion of the acid polymer as it is neutralized leaving little if any of the alkaline solution to convert the remaining unneutralized acid polymer particles to their salt form.

Thus, the aqueous alkaline solution employed for neutralization is formulated to contain an amount of base which will achieve the proper degree of salting when the aqueous solution is applied at a rate sufficient to maintaining proper moisture control. In addition to a suitable base, the aqueous alkaline solution can also contain wetting agents, i.e. surfactants, in amounts sufficient to achieve a deposit in the composite product of up to about 5% by weight, based on the weight of the polymer contained in the composite. Suitable surfactants include nonionic agents such as the polyalkylene derivatives of propylene glycol available under the trade name of Pluronics TM, and the alkali metal salts of sulfosuccinate esters such as sodium dioctyl sulfosuccinate available under the trade name Aerosol-OT TM.

The amount of base selected to be present in the aqueous solution will depend in part on the rate at which the aqueous solution is applied which in turn will depend on the method adopted for applying the aqueous solution to the composite.

The aqueous alkaline solution can be applied to the composite in a variety of methods common to the paper coating industry. For example, such techniques include the use of a three roll configuration known as the reverse roll coater, the use of spray coating, and a blade coater or dip coater.

Typically, the composite is conveyed through a bath or spray of the aqueous alkaline solution. At a given rate of passage through the bath or spray if the amount of base in the aqueous solution is too low insufficient degree of salting will result. If the amount of base in the aqueous solution is too high the rate of conversion of the polymer from the acid form to the salt form is so rapid that the residence time in the bath must be reduced to the extent that accurate control of the balance between the degree of salting and water content is rendered extremely difficult. If the proper balance is not achieved and the residence time in the aqueous bath or spray is too long, excessive amounts of water will be sorbed by the polymer component during neutralization.

To prevent this from occuring the composite product, e.g. wet-laid web, is monitored to assure that the proper balance of degree of salting and moisture sorption is achieved. The degree of salting can be controlled by testing the pH of the composite after sufficient time has elasped for the base to completely react with the polymer component. Typically this occurs after the neutralized composite has been dried in accordance with the drying step described below. The pH of the composite can be determined by applying an appropriate indicator to a portion of the web thereof as it exits the dryer. Alternatively the pH can be tested by saturating the composite in excess water and testing the pH of the water with a pH meter. The moisture content of the composite can be determined by weighing a sample thereof after it exits the neutralizing zone when wet and when dry. The rate of passage through the neutralizing bath or spray is then controlled based on the pH and moisture content information to achieve the proper balance between degree of salting and moisture sorption.

In a preferred embodiment the degree of salting and moisture sorption is monitored in a single step by measuring the thickness of the composite as it exits the neutralizing zone. It has been found that the composite swells in proportion to the amount of water which is sorbed during neutralization and that the degree of swelling can also accurately indicate whether the proper degree of salting has been achieved since the latter directly affects the ability of the composite to sorb water. Consequently, the thickness of the composite after neutralization is calibrated as a function of the concentration of the base in the aqueous alkaline solution employed for neutralization and as a function of the residence time of the composite in said solution for a given base concentration. This can be achieved by observing the change in thickness (using the dry composite as a reference point) of the composite at various concentrations of base and at varying residence times within the aqueous alkaline solution. The pH and moisture content of the composite after neutralization can then be determined, as described above, for each set of base concentrations and residence time parameters. Thus, after proper thickness calibration the rate of travel of the composite through the aqueous alkaline solution, wherein the base is present at a given concentration, is controlled in response to signals from a sensing means which measures the thickness of the composite as its exits the neutralization zone.

In calibrating the thickness of the composite, typically the pH thereof after complete neutralization should not be greater than about 9 nor less than about 7.

The residence time in the aqueous alkaline solution, the rate of travel therethrough, the length of the contact zone, and the concentration of the base therein will vary depending on the initial thickness of the composite, the type of base employed, and the density of the composite neutralized. Control of these variables will be obvious to one skilled in the art based on the description provided herein and in the examples.

Means for sensing the thickness of the neutralized composite are well known and include such devices as a Beta gauge. The rate of travel of the composite through the neutralizing zone can be controlled manually or automatically in response to a feed back signal from the sensing means.

Preferably, the composite is supported on a porous fabric belt of polyester or nylon as it travels through the neutralizing spray or bath to reduce the possibility of composite slippage, tearing and breaks which can occur therein during the neutralizing step.

Upon completion of the neutralizing step the composite is passed through a drying zone in accordance with conventional paper making procedures to reduce the moisture content therein to not greater than about 25%, preferably not greater than about 20%, and most preferably not greater than about 15%, by weight, based on the weight of the composite including water. Preferred drying temperatures may vary from about 25° to about 150° C., and most preferably from about 80° to about 110° C.

Because the amount of water sorbed during neutralization is controlled, it is an advantage of the present invention that the amount of water which is removed in the final drying step is less than the amount of water employed in the direct neutralization of the polymer alone and is in the range or only slightly higher than that amount which is removed in conventional paper making operations during the conventional drying step.

It is to be understood that while the above description is directed to the preparation of a single composite the described process can be modified to obtain shaped articles of greater thickness. For example, a plurality of neutralized composite sheets may be formed and superimposed one on the other. These are then laminated between pressure rollers to obtain a multiple thickness, or slightly less because of slight spread under lamination pressure.

It is to be further understood that the neutralizing step of the presently described process can be conducted on a continuous on-line basis or on a batch off-line basis wherein the partially dried composite is collected on a roll and neutralized at a later time.

The composite products, particularly composite sheets formed in the process of the present invention may be used in a number of ways to manufacture highly sorbent pads, sheets, and other shaped forms. As such they are particularly useful for the manufacture of diapers, household and industrial wipes, sanitary napkins, tampons, surgical sponges and the like. The composite sheets have an advantage over other sorbent products which employ other particulate water swellable polymers in that after water sorption, the product still maintains its particulate form, albeit highly swollen. Super sorbing polymers known to the art become viscous, soft amorphous gels at high swelling ratios. The polymer components of the composite sheet described herein are accordingly non-blocking and therefore will rapidly sorb large quantities of an aqueous fluid as the fluid rapidly penetrates into a mass of particles. Of particular importance, in addition, is the composite sheet's ability to be used in the manufacture of non-woven fabrics and sheets which employ dry carding operations. For example, in the manufacture of non-wovens containing cellulose fibers, the cellulose is received in the form of a so called wet lap roll. This dry blotter-like roll is ground in dry pulverizing equipment to separate the cellulose fibers and form a bulky cotton-like mass. These fibers are then fed along with other fiber components, e.g. cotton, rayon, rag, and synthetics, to a carding, blending and sheet forming machine e.g. a Curolator, and the composite non-woven is formed. On a laboratory scale, a Waring Blendor will reduce the wet lap sheet to a defiberized mass within a few minutes. The composite super sorbing polymer-cellulose composite formed in accordance with the process described herein may be similarly treated. Three to five minutes in a Waring Blendor are sufficient to reduce it to a cotton-like mass. Microscopic examination shows the polymer still to be adherent to the cellulose fiber. The fibers can then be introduced into a Curolator along with other fibers and a composite made without loss of polymer.

The present invention is further illustrated by the following examples. All parts and percentages in the examples as well as in the specification and claims are by weight unless otherwise specified.

EXAMPLE 1

PART A

Preparation of Polymer Component of the Paper Furnish

A copolymer of methyl acrylate (MA) and methacrylic acid (MAA) crosslinked with ethylene glycol dimethacrylate (EDMA) is prepared by the suspension polymerization technique wherein the monomer weight ratio of MA/MAA/EDMA employed is 65/35/0.1.

More specifically, polymerization reactor is charged with 2,000 grams of deionized water and 3 grams of Cellosize QP-4400 (product of Union Carbide which is a hydroxyethyl cellulose powder having a 2% viscosity of 4,000 to 6,000 cps) as suspending agent. The contents of the reactor are heated to 65° C. until the hydroxyethyl cellulose dissolves and then cooled to 35° C.

To the reactor is then added with agitation, a mixture containing 325 grams methyl acrylate, 175 grams glacial methacrylic acid, 0.5 grams ethylene glycol dimethacrylate as crosslinking agent and 0.5 grams azobisisobutyronitrile as catalyst. The contents of the reactor are deaerated by purging with nitrogen which is passed therethrough at a moderate flow rate (e.g., 100 milliliters per minute). The temperature is raised to 70° C. and the mixture allowed to polymerize for three hours. In the last hour the reactor temperature is raised to 80° C. to complete the reaction. The total reaction time is three hours. The contents of the reactor are continuously agitated during the entire polymerization reaction.

Upon completion of the reaction, the reactor slurry is cooled to 25° C. and filtered by passing the slurry through a vacuum filter. The solids content of the filter cake is 66%.

Sufficient amount of filter cake and water are added to a Waring Blendor and agitated for 3 to 5 minutes to make a 10% finely divided polymer slurry in water.

PART B

Preparation of Furnish and Wet-Laid Web

Rayfloc J alpha cellulose pulp and the polymer slurry prepared in accordance with part A are proportioned to a conventional hydropulper to yield a slurry wherein the solids content of the slurry is about 2.0% and the solids comprise about 65%, by weight, Rayfloc J and 35% polymer. The furnish is beaten in a Hollander beater to a Canadian Standard Freeness of between 150 and 180 ml and the polymer is suspended. 1.0% by weight based on the fiber weight, of alum is also added to the beater to clean up the white water of the cellulose fines. The furnish is then passed to a stuff box and then to a dilution box where the furnish is diluted with water to a solids content of 0.38 to 0.40% by weight. From the dilution box the furnish is passed to a headbox. The headbox is set to give a paper of 14 gms/sq.ft. The diluted furnish is delivered to the foraminous support of a conventional Fourdrinier machine which is moving at a rate of 42 ft/minute. The wet-laid web is passed through a press section containing 2 nip rolls and then through two drying ovens located in series. The composite sheet is dried to a moisture content of 4.11%, by weight thereof, and wound up on a take-up roll. The sheet contains 32.9% polymer and 67.1% Rafloc J.

The resulting sheet is then neutralized in an off-line operation as follows.

The equipment employed consists of a coating or impregnation section, followed by a Beta gauge for measuring change in wet thickness as sodium hydroxide is picked up by the sheet and finally a 16 foot moving belt tunnel drier leading to a wind-up roll. The system and rate of travel is driven by tension arising at the wind-up roll. The drier belt and rolls of the coater are separately driven to synchronize with the wind-up roll. The coating or saturation section consists of 3" diameter steel, plastic, and rubber rolls which can be arranged in a variety of ways to assist sheet travel and lead the sheet down into and out of a coating trough containing an aqueous alkaline solution. In the coating section, the paper sheet is passed about the steel roll through a bath containing water, 2.0%, by weight NaOH, and 0.41% Aerosol OT-75 (cloudy precipitate and separation of 2-ethylhexyl alcohol are minimized under these conditions) and over and about the plastic roll which is immersed in the bath. The sheet is then passed up out of the bath and over and about the rubber roll. After passing over the rubber roll of the coating section, the sheet is passed unsupported for approximately 6 feet, first passing through the plates of a Tracer Lab Beta gauge and then into the drier belt and final wind-up.

The Beta gauge is then calibrated by varying the rate of travel of the sheet through the bath. The degree of salting is determined for each run as well as the wet pick-up of the solution expressed as the ratio of the weight of a sample of the wet sheet immediately after neutralization to the dry weight of the same sample. The degree of salting and associated wet pick-up ratios are summarized at Table I. A series of dipping experiments are then conducted wherein the residence time in the alkaline solution bath is varied for periods ranging from 1 second to 6 seconds and wet pick-up ratios, corresponding Beta meter readings are taken on the wet sheets. A plot of the Beta gauge readings vs. wet pick-up ratios is then used as the basis for controlling the degree of neutralization during the run. The results of the calibration are summarized at Table II.

From this data the Beta gauge readings of 254, 228 and 200 are determined to represent degrees of salting of 100%, 110%, and 120%.

After calibration of the Beta gauge it is decided to make a neutralization run to achieve degrees of salting of 110±10%. The residence time in the bath is controlled to be between 4 and 10 seconds. The length of the contact zone is 4"-6" and the rate of travel varies from 3 to 6 ft/min. More specifically, the Beta gauge is initially set at a null point to give 110±10% degree of salting. The rate of travel and the depth of liquid in the trough (contact zone control) are then adjusted manually attempting to keep the Beta gauge reading as close to the null point as possible. A run of paper is started by drawing the paper at 6-10 ft/minute with the dipping roll raised out of the bath. The assembly is then lowered into the bath and the rate of travel is gradually reduced to about 3 ft/minute, using the Beta gauge as a guide. Once all conditions are adjusted the Beta gauge swings are held to within the desired range of about ±15 for runs of 10-20 feet of paper at a time. However, because of mechanical problems of synchronization and slippage of the sheet on the roll, instances can occur where the sheet lags behind in the treatment bath. This resuts in excess liquid sorption and consequent tearing of the sheet, necessitating renewed start-up. Slippage and tearing can be eliminated by supporting the sheet on an endless porous fabric belt as it travels through the treating bath. This would also permit the preparation of thinner sheets.

The composite sheet is then passed twice through a drying oven maintained at 250° F.

Samples from the sheet are tested for degree of salting using a pH meter and it is found to be within the range of 110±10%. Several samples are taken from the sheet and evaluated for swelling by placing the samples in a solution of 1% NaCl until the weight thereof reaches equilibrium. Each sample is then placed under a weight to apply a pressure of 1.5 psi to simulate the pressure which would be applied by an infant wearing a diaper. The wet pick-up for several samples is then determined and the average weight of the wet samples is found to be 8.45 times the dry weight of the samples. The average pH of the samples is about 8.7.

It is also determined that the water evaporated after neutralization is in the range of 2.6 to 3.0 lbs/lb of dried product which is within the range of conventional paper. An additional 1-2 lbs/lb of water is removed during the original paper making step which brings the total amount of water evaporated in the process to between 3.7 and 5 lbs/lb of paper product.

TABLE I

| Run No. | Degree of Salting (%) | Wt. of Wet Sheet Sample/Wt. of Dry Sheet Sample |
|---|---|---|
| 1 | 80 | 3.14 |
| 2 | 90 | 3.40 |
| 3 | 100 | 3.67 |
| 4 | 110 | 3.93 |
| 5 | 120 | 4.20 |
| 6 | 130 | 4.47 |
| 7 | 140 | 4.73 |
| 8 | 150 | 5.00 |

TABLE II

| Run No. | Residence In Bath (Sec) | Initial Dry Wt. 4" × 9" Sample (gms) | Wet Wt. After Neutral-ization | Ratio of Wet Wt.: Dry Wt. | Ratio of Base Sol. Pick-Up: Dry Wt. | Degree of Salting (%) | Beta Guage Reading |
|---|---|---|---|---|---|---|---|
| 1 | 0 | Air Dried Sheet | | | | 0 | 699 |
| 2 | 1 | 3.51 | 12.06 | 3.43/1.0 | 2.43/1.0 | 90 | 254 |
| 3 | 2 | 3.57 | 12.52 | 3.51/1.0 | 2.51/1.0 | 94.1 | 267 |
| 4 | 4 | 3.59 | 15.54 | 4.22/1.0 | 3.22/1.0 | 120 | 238 |
| 5 | 6 | 3.61 | 16.59 | 4/70/1.0 | 3.70/1.0 | 140 | 162 |

EXAMPLE 2

Several samples of the unneutralized composite sheets employed in Example 1 are neutralized in this embodiment by dipping them individually in any one of these solutions containing 1.5, 2.0, and 3.0% NaOH respectively. It is found that it takes a 7 second immersion in the 2% aqueous alkaline solution to achieve a degree of salting of 120%. A bone-dry paper requires 8.5 seconds to achieve the same degree salting. When the 1.5% NaOH aqueous solution is employed it is found that the base necessary to achieve 120% degree of salting could not be absorbed within 20 seconds. When a 3% NaOH aqueous solution is employed the residence time in the bath sufficient to achieve a degree of salting of 120% is about 2–3 seconds. This residence time is too short and too difficult to control accurately. Yellowing of the paper is also a problem at this concentration.

This example illustrates the effect of controlling the base concentration and the effect of complete drying instead of partial drying.

EXAMPLE 3

5"×8" sheets of unneutralized composite sheets prepared in accordance with Example 1 are dipped in a 2% NaOH aqueous solution. The residence time of each sheet in the solution is varied as shown at Table III. The samples are air dried except for run 6 which is dried at a temperature of 80°–90° C. for 30 minutes. The degree of salting achieved for each sample is determined from the amount of caustic pick-up and the results are also summarized at Table III. The degree of swelling of each sample is determined in accordance with Example 1 under an applied pressure of 1.5 psi. The pH of several of the samples is also determined. The proportional contribution of the polymer component of the sheet to the total degree of sorption by the neutralized sheet expressed as a multiple of the dry weight of the sheet is also shown at Table III. Note that the polymer contribution of runs 3 and 5 is greater than is ordinarily observed for the polymer alone which is in the range of 18–20×. This is believed to be due to surface sorption and capillary effects in the sheet.

TABLE III

| Run No. | Residence Time (Sec) | Degree of Salting (%) | Wet Pick-Up Wt./Dry Wt. of Sample | Polymer Contribution[1] | pH |
|---|---|---|---|---|---|
| 1 |  | 79% | 5.6X | 12.9X | ND |
| 2 | 2 | 82% | 6.3:1 | 15.1X | ND |
| 3 | 4 | 100% | 8.9:1 | 22.9X | ND |
| 4 | 6 | 106% | 8.5:1 | 21.8X | 7.3 |
| 5 | 8 | 114% | ND | 24.8X | ND |
| 6 | 10 | 113% | 9.5:1 | ND | 8.0 |
| 7 | 15 | 136% | 8.7:1 | 22.4X | 9.7 |
| 8 | 20 | 148% | 8.6:1 | 22.1X | 9.1 |

ND = Not determined.

[1] Polymer contribution expresses the fractional contribution of the polymer component to the total absorption of the sheet based on the determination that a sheet containing no polymer component will absorb 2.0 times its weight in water. Polymer contribution is determined from the following equation:

$$(2.0)(0.67) + (0.329)(PC) = (\text{wt. pick-up wt./dry wt. of sample})$$

wherein PC is the polymer contribution. The polymer contribution indicates the multiple by which the polymer component weight is increased by the sorption of water from the treating solution.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for preparing a water sorptive product which comprises:
   (1) forming an aqueous suspension comprising a slurry of a potentially water swellable, water-insoluble polymer component and a fibrous component in water wherein the polymer component comprises the reaction product of:
      (a) from about 15% to about 50% by weight of an olefinically-unsaturated carboxylic acid;
      (b) from about 49.07% to about 82% by weight of an alkyl acrylate wherein the alkyl group has from 1 to 6 carbon atoms; and
      (c) from about 0.03% to about 3.0% by weight of a crosslinking agent, said reaction product having carboxyl groups present therein which when coverted to their salt form maintains the polymer water-insoluble and imparts the capability of said polymer component of sorbing water upon contact therewith; and
   wherein the fibrous component comprises at least 50% cellulose material, and the weight ratio of said polymer component to said fibrous component is controlled to from about 90:10 to about 5:95;
   (2) forming a composite product from said suspension;
   (3) partially drying said composite product to reduce the moisture content thereof to between about 3 and about 25%, by weight, based on the weight thereof;
   (4) contacting said partially dried composite product with an amount of an aqueous solution of a base sufficient to achieve a degree of salting of the polymer component of said composite product of from about 100 to about 120% and thereby netralize the carboxylic groups present thereon and in a manner sufficient to prevent the weight ratio of the dry neutralized composite product to water sorbed therein from exceeding 1:10 without solubilizing the polymer salt; and
   (5) drying said neutralized composite product to reduce the moisture content thereof to not greater than about 25% by weight.

2. The process of claim 1 wherein (1) the polymer component is the reaction product of from about 20 to about 40% by weight of at least one olefinically-unsaturated carboxylic acid selected from the group consisting of methacrylic acid and acrylic acid, about 59.02 to about 78% by weight of at least one alkyl acrylate selected from the group consisting of methyl acrylate, ethyl acrylate and n-butyl acrylate, and from about 0.08 to about 2% by weight of at least one crosslinking agent selected from the group consisting of diacrylate glycol esters, dimethacrylate glycol esters, diacrylate, polyether glycols, dimethacrylate ether glycol esters, allyl esters of polymerizable unsaturated carboxylic acids, di and tri vinyl aromatic compounds, di and triallyl esters of di and tribasic acids, and acrylate and methacrylate polyol esters; and (2) the fibrous component comprises at least 50% by weight cellulose fibers and the remainder is optionally comprised of at least one other natural or synthetic fiber.

3. The process of claim 2 wherein the weight ratio of the polymer component to the fibrous component in the suspension is controlled to be from about 65:35 to about 15:85.

4. The process of claim 1 wherein the composite product is at least one composite sheet.

5. The process of claim 1 wherein the degree of salting is controlled to be from about 110 to about 120% and the weight ratio of the dry neutralized composite product to water sorbed therein immediately after neutralization is controlled to be from about 1:0.5 to about 1:5.0.

6. A process for preparing a composite sheet having water sorptive properties which comprises:
  (1) depositing a suspension comprising a slurry of a polymer component and a fibrous component in water on a liquid permeable support to form a wet-laid web wherein said polymer component is a potentially water swellable, water-insoluble polymer comprises the reaction product of:
    (a) from about 15% to about 50% by weight of an olefinically-unsaturated carboxylic acid;
    (b) from about 49.07% to about 82% by weight of an alkyl acrylate wherein the alkyl group has from 1 to 6 carbon atoms; and
    (c) from about 0.03% to about 3.0% by weight of a crosslinking agent; said reaction product having carboxyl groups present thereon which when converted to their salt form maintains the polymer water-insoluble and imparts the capability to said polymer component of sorbing water upon contact therewith;
  and wherein said fibrous component comprises at least 50% by weight of cellulose fibers and the weight ratio of said polymer component to said fibrous component is controlled to be from about 90:10 to about 5:95;
  (2) passing said wet-laid web through a drying zone wherein the moisture content is reduced to between about 3 and about 25% by weight thereof;
  (3) passing said wet-laid web through a neutralizing zone wherein it is contacted with an aqueous alkaline solution containing a base in an amount sufficient to achieve a degree of salting of the polymer component of from about 100 to about 120% and thereby neutralize the carboxyl groups present thereon causing the polymer component to swell and increase in thickness from sorption of water without solubilizing the polymer salt;
  (4) sensing the thickness of the neutralized wet-laid web as it exits the neutralizing zone;
  (5) controlling the rate of travel of said wet-laid web through the neutralizing zone in response to the sensed wet-laid web thickness in a manner sufficient to prevent the weight ratio of the dry neutralized wet-laid web to water sorbed therein after exiting the neutralizing zone from exceeding 1:10;
  (6) passing the neutralized wet-laid web through a drying zone wherein the moisture content thereof is controlled to be not greater than about 25% by weight.

7. The process of claim 6 wherein (1) the polymer component is the reaction product of from about 20 to about 40% by weight of at least one olefinically-unsaturated carboxylic acid selected from the group consisting of methacrylic acid and acrylic acid, about 59.02 to about 78% by weight of at least one alkyl acrylate selected from the group consisting of methyl acrylate, ethyl acrylate and n-butyl acrylate, and from about 0.08 to about 2% by weight of at least one crosslinking agent selected from the group consisting of diacrylate glycol esters, dimethacrylate glycol esters, diacrylate polyether glycols, dimethacrylate ether glycol esters, allyl esters of polymerizable unsaturated carboxylic acids, di and tri vinyl aromatic compounds, di and triallyl esters of di and tribasic acids, the acrylate and methacrylate polyol esters; and (2) the fibrous component comprises at least 50% by weight cellulose fibers and the remainder is optionally comprised of at least one other natural or synthetic fiber.

8. The process of claim 6 wherein the degree of salting is controlled to be from about 110 to about 120% and the weight ratio of the dry neutralized composite product to water sorbed therein immediately after neutralization is controlled to be from about 1:0.5 to about 1:5.0.

9. The process of claim 6 wherein the weight ratio of the polymer component to the fibrous component in the suspension is controlled to be from about 65:35 to about 15:85.

* * * * *